United States Patent [19]

Ledouble et al.

[11] 4,316,854
[45] Feb. 23, 1982

[54] PROCESS FOR THE PRODUCTION OF BIS-[0-(1-ALKYLTHIOETHYLIMINO)-N-METHYLCARBAMYL]-N,N-SULFIDES

[75] Inventors: Jean-Pierre Ledouble, Rosenau, France; Klaus Müller, Reinach, Switzerland

[73] Assignee: Ciba-Geigy Corporation, Ardsley, N.Y.

[21] Appl. No.: 156,966

[22] Filed: Jun. 6, 1980

[30] Foreign Application Priority Data

Jun. 18, 1979 [CH] Switzerland .................. 5669/79

[51] Int. Cl.³ ............................................. C07C 119/18
[52] U.S. Cl. .................................................. 260/453.1
[58] Field of Search ..................... 260/453 RW, 453.1

[56] References Cited

U.S. PATENT DOCUMENTS 4,004,031  1/1977  Drabek .

OTHER PUBLICATIONS

Weast, Handbook of Chemistry and Physics, 60th ed., Chem. Rubber Co. Press, p. E-64.
Noller, Textbook of Organic Chemistry, 2nd Edition, W. B. Saunders Company, Philadelphia, 1958, p. 153.

Primary Examiner—John M. Ford
Assistant Examiner—Robert C. Whittenbaugh
Attorney, Agent, or Firm—Karl F. Jorda

[57] ABSTRACT

A process for the production of bis-[0-(1-alkylthioethylimino)-N-methylcarbamyl]-N,N'-sulfides of the formula

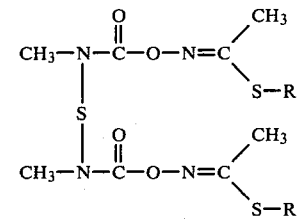

wherein R is a straight-chain or branched alkyl group of 1 to 5 carbon atoms, by reaction of a 0-(1-alkylthioethylimino)-N-methylcarbamate of the formula

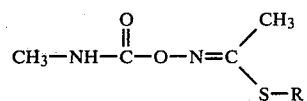

in the presence of a base, with sulfur dichloride or sulfur monochloride, in a solvent having a dielectric constant of 2.0 and a dipole moment of 0 to 1, is described.

The bis-[0-(1-alkylthioethylimino)-N-methylcarbamyl]-N,N'-sulfides of the above formula possess insecticidal properties and are suitable in particular for controlling pests of cotton plants and bluebottles.

9 Claims, No Drawings

PROCESS FOR THE PRODUCTION OF BIS-[0-(1-ALKYLTHIOETHYLIMINO)-N-METHYLCARBAMYL]-N,N-SULFIDES

The present invention relates to a process for the production of bis-[0-(1-alkylthioethylimino)-N-methylcarbamyl]-N,N'-sulfides of the formula

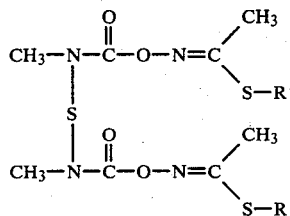

wherein R is a straight-chain or branched alkyl group of 1 to 5 carbon atoms, by reacting a 0-(1-alkylthioethylimino)-N-methylcarbamate of the formula

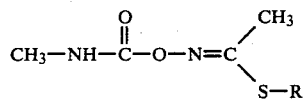

wherein R is as defined above, in the presence of a base, with sulfur dichloride or sulfur monochloride.

The bis-[0-(1-alkylthioethylimino)-N-methylcarbamyl]-N,N'-sulfides of the formula I possess insecticidal properties and are useful in particular for controlling pests of cotton plants and bluebottles (*Lucilia sericata*).

It is already known from German Offenlegungsschrift No. 2 530 439 to obtain the bis-[0-(1-alkylthioethylimino)-N- methylcarbamyl]-N,N'-sulfides of the formula I by reaction of a 0-(1-alkylthioethylimino)-N-methylcarbamate of the formula II in an inert solvent and in the presence of a base, in the temperature range from −10° to 100° C., with sulfur dichloride or sulfur monochloride. As suitable inert solvents for this reaction, mention is made of ethers, aliphatic and aromatic hydrocarbons and ketones, while suitable bases are in particular tertiary amines such as trialkylamines, pyridines, and N,N-dialkylanilines. The drawback of this method is that the reaction does not proceed uniformly when using the above solvents, resulting in a diminution of the yield and quality of the product. In addition, lengthy reaction times are necessary.

It has now been found that the above disadvantages can be overcome by carrying out the reaction of the 0-(1-alkylthioethylimino)-N-methylcarbamate of the formula II with sulfur dichloride or sulfur monochloride, in the presence of a base, in a solvent having a dielectric constant of 2.0 to 2.5 and a dipole moment of 0 to 1.

In the practice of this invention, it is possible to use, as solvents, pure nonpolar solvents or mixtures of nonpolar solvents with polar solvents having the properties specified above. Suitable nonpolar solvents are halogenated hydrocarbons such as carbon tetrachloride, 1,1,2-trifluoro-1,2,2-trichloroethane (Flugen ® 113) and tetrachloroethylene. Suitable mixtures of nonpolar solvents and polar solvents are mixtures of carbon tetrachloride with chloroform or 1,2-dichloroethane, mixtures of hexane with methylene chloride or 1,2-dichloroethane, as well as mixtures of benzene or cyclohexane with 1,2-dichloroethane.

In the above mixtures of nonpolar and polar solvents, the amount of polar solvent must always be so chosen that the mixture has a dielectric constant of 2.0 to 2.5 and a dipole moment of 0 to 1. To accomplish this, the amount of polar solvent is between 2 and 20% by volume, depending on its polarity.

Especially good results are obtained by using 1,1,2-trifluoro-1,2,2-trichloroethane or tetrachloroethylene as solvent. The use of these solvents is therefore preferred, with 1,1,2-trifluoro-1,2,2-trichloroethane being especially preferred.

The solvents to be used in the practice of this invention are used in amounts of 500 to 1000 ml, preferably 500 to 700 ml, per mole of 0-(1-alkylthioethylimino)-N-methylcarbamate of the formula II.

Suitable bases in the presence of which the reaction of 0-(1-alkylthioethylimino)-N-methylcarbamates of the formula II with sulfur dichloride or can be carried out, are pyridine, alkylpyridines such as picoline and lutidine, and N,N-dialkylanilines which are substituted in the para-position by halogen, alkyl or alkoxy. The preferred base is pyridine.

The above bases can be employed in stoichiometric amount or in an excess of up to 100%. It is preferred to employ an excess of 50%, based on the stoichiometric amount.

The reaction of an 0-(1-alkylthioethylimino)-N-methylcarbamate of the formula II with sulfur dichloride or sulfur monochloride is carried out in the temperature range from −10° to 50° C., with the preferred range being from 0° to 30° C., and takes 2 to 10 hours and often only 4 to 6 hours.

In a preferred embodiment, the process of the invention is carried out by first adding the base, preferably pyridine, with cooling, to a ready prepared mixture of sulfur dichloride or sulfur monochloride and the solvent, preferably 1,1,2-trifluoro-1,2,2-trichloroethane, and then adding the 0-(1-alkylthioethylimino)-N-methylcarbamate of the formula II, and keeping the reaction mixture for 4 to 6 hours at a temperature in the range from 0° to 30° C.

The starting 0-(1-alkylthioethylimino)-N-methylcarbamates of the formula II are known from British patent specification No. 1 138 347. They can be produced e.g. by reaction of acetaldehyde with hydroxylamine to give acetaldoxime, further reaction of the acethydroxyamyl chloride obtained by chlorination of acetaldoxime with alkali alkylmercaptide to give the corresponding 1-alkylthioacetaldoxime, and further reaction of this latter with methyl isocyanate.

The process of the present invention makes it possible to obtain the bis-[0-(1-alkylthioethylimino)-N-methylcarbamyl]-N,N'-sulfides of the formula I in yields between 80 and 85% of theory, while substantially avoiding the formation of undesirable by-products. The final products are obtained in a purity of 95% and can be used without further purification. In addition, the use of the solvent proposed in the practice of this invention makes it possible to shorten the reaction time to less than 10 hours. The process of the invention is therefore most suitable for the production of the insecticidal compounds of the formula I on an industrial scale.

The following Examples illustrate the process of the invention in more detail.

EXAMPLE 1

31.0 g (0.30 mole) of sulfur dichloride are added to 285 ml of 1,1,2-trifluoro-1,2,2-trichloroethane (Flugen ® 113). With stirring, 55.0 g of pyridine are then added dropwise to the above mixture at 5° to 10° C. When the addition of pyridine is complete, 75.0 g (0.46 mole) of 0-(1-methylthioethylimino)-N-methylcarbamate are added at 10° C. The reaction mixture is then warmed to 30° C. and stirred for 4 hours at this temperature. The mixture is then filtered and the filter residue is stirred with water. The product is collected once more by filtration, and dried at 40° C. in vacuo, affording 69.0 g of bis-[0-(1-methylthioethylimino)-N-methylcarbamyl]-N,N'-sulfide in 95% purity, corresponding to a yield of 80% of theory, based on 0-(1-methylthioethylimino)-N-methylcarbamate.

EXAMPLE 2

31.0 g (0.3 mole) of sulfur dichloride and 75 g (0.46 mole) of 0-(1-methylthioethylimino)-N-methyl-carbamate are reacted in 325 ml of tetrachloroethylene in accordance with the method described in Example 1, except that the reaction mixture is stirred for 5 hours at 30° C. after the addition of 0-(1-methylthioethylimino)-N-methylcarbamate.

Yield: 69.0 g of 95% bis-[0-(methylthioethylimino)-N-methylcarbamyl]N,N'-sulfide, corresponding to 80% of theory.

What is claimed is:

1. In a process for the production of bis-[0-(1-alkylthioethylimino)-N-methylcarbamyl]-N,N'-sulfides of the formula

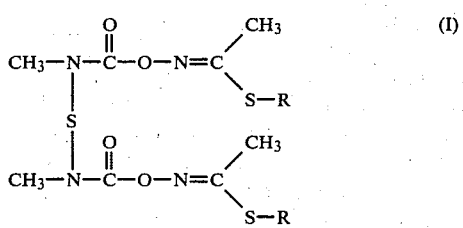

wherein R is a straight-chain or branched alkyl group of 1 to 5 carbon atoms, by reacting a 0-(1-alkylthioethylimino)-N-methylcarbamate of the formula

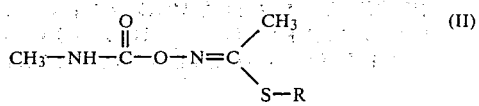

wherein R is as defined above, in the presence of a base, with sulfur dichloride or sulfur monochloride in an inert solvent, the improvement which comprises using a halogenated hydrocarbon as solvent with a dielectric constant of 2.0 to 2.5 and a dipole moment of 0 to 1.

2. A process according to claim 1, wherein the solvent is carbon tetrachloride, 1,1,2-trifluoro-1,2,2-trichloroethane, or tetrachloroethylene.

3. A process according to claim 1, wherein the solvent is 1,1,2-trifluoro-1,2,2-trichloroethane or tetrachloroethylene.

4. A process according to claim 1, wherein the solvent is 1,1,2-trifluoro-1,2,2-trichloroethane.

5. A process according to claim 1, wherein the solvent is used in amounts of 500 to 1000 ml per mole of 0-(1-alkylthioethylimino)-N-methylcarbamate of the formula II.

6. A process according to claim 1, wherein the solvent is used in amounts of 500 to 700 ml per mole of 0-(1-alkylthioethylimino)-N-methylcarbamate of the formula II.

7. A process according to claim 1, wherein the reaction of a 0-(1-alkylthioethylimino)-N-methylcarbamate of the formula II with sulfur dichloride or sulfur monochloride is carried out in the presence of pyridine.

8. A process according to claim 1, wherein the reaction of a 0-(1-alkylthioethylimino)-N-methylcarbamate of the formula II with sulfur dichloride or sulfur monochloride is carried out in the temperature range from −10° to +50° C., preferably from 0° to 30° C.

9. A process according to claim 1 which comprises carrying out the reaction of a 0-(1-alkylthioethylimino)-N-methylcarbamate of the formula II with sulfur dichloride or sulfur monochloride by first adding the base, with cooling, to a ready prepared mixture of the sulfur dichloride or sulfur monochloride and the solvent, then adding the 0-(1-alkylthioethylimino)-N-methylcarbamate of the formula II, and keeping the reaction mixture for 4 to 6 hours at a temperature in the range from 0° to 30° C.

* * * * *